US006657109B1

(12) United States Patent
Perry

(10) Patent No.: US 6,657,109 B1
(45) Date of Patent: Dec. 2, 2003

(54) INBRED MAIZE LINE NP2015

(75) Inventor: Christopher O. Perry, Northfield, MN (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/241,585

(22) Filed: Feb. 2, 1999

(51) Int. Cl.⁷ .............................. A01H 5/00; A01H 1/00; A01H 1/02; C12N 5/04; C12N 5/00
(52) U.S. Cl. ..................... 800/320.1; 435/412; 435/410; 435/419; 800/275; 800/271; 800/303; 800/298
(58) Field of Search ................................ 800/320.1, 275, 800/271, 303, 298; 435/412, 410, 419

(56) References Cited

PUBLICATIONS

Phillips et al. Corn and Corn Improvment. 1988. Agronomy Monograph No. 18, 3rd edition. Chapter 5, pp. 345–368.*

* cited by examiner

*Primary Examiner*—Lynette R. F. Smith
*Assistant Examiner*—Ousama Zaghmout
(74) *Attorney, Agent, or Firm*—Bruce Vrana

(57) ABSTRACT

An inbred maize line, designated NP2015, the plants and seeds of inbred maize line NP2015, methods for producing a maize plant produced by crossing the inbred line NP2015 with itself or with another maize plant, and hybrid maize seeds and plants produced by crossing the inbred line NP2015 with another maize line or plant.

42 Claims, No Drawings

INBRED MAIZE LINE NP2015

FIELD OF THE INVENTION

This invention is in the field of maize breeding, specifically relating to an inbred maize line designated NP2015.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like. Hybrid maize seed is typically produced by a male sterility system incorporating manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile maize and CMS produced seed of the same hybrid can be blended to insure that adequate pollen loads are available for fertilization when the hybrid plants are grown. There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5; etc.

A single cross maize hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

The development of a maize hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). Much of the hybrid vigor exhibited by F1 hybrids is lost in the next generation (F2). Consequently, seed from hybrids is not used for planting stock.

Hybrid seed production requires elimination or inactivation of pollen produced by the female parent. Incomplete removal or inactivation of the pollen provides the potential for self pollination. This inadvertently self pollinated seed may be unintentionally harvested and packaged with hybrid seed. Once the seed is planted, it is possible to identify and select these self pollinated plants. These self pollinated plants will be genetically equivalent to the female inbred line used to produce the hybrid. Typically these self pollinated plants can be identified and selected due to their decreased vigor. Female selfs are identified by their less vigorous appearance and/or reproductive characteristics, including shorter plant height, small ear size, ear and kernel shape, cob color, or other characteristics.

Identification of these self pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritca si Aplicata Vol. 20 (1) p. 29–42.

As is readily apparent to one skilled in the art, the foregoing are only two of the various ways by which the inbred can be obtained by those looking to use the germplasm. Other means are available, and the above examples are illustrative only.

Maize is an important and valuable field crop. Thus, a continuing goal of plant breeders is to develop high-yielding maize hybrids that are agronomically sound based on stable inbred lines. The reasons for this goal are obvious: to maximize the amount of grain produced with the inputs used and minimize susceptibility of the crop to pests and environmental stresses. To accomplish this goal, the maize breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. The probability of selecting any one individual with a specific genotype from a breeding cross is infinitesimal due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder.

Thus, even if the entire genotypes of the parents of the breeding cross were characterized and a desired genotype known, only a few, if any, individuals having the desired genotype may be found in a large segregating F2 population. Typically, however, neither the genotypes of the breeding cross parents nor the desired genotype to be selected is known in any detail. In addition, it is not known how the desired genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new maize inbred line.

SUMMARY OF THE INVENTION

According to the invention, there is provided a novel inbred maize line, designated NP2015. This invention thus relates to the seeds of inbred maize line NP2015, to the plants of inbred maize line NP2015, and to methods for producing a maize plant by crossing the inbred line NP2015 with itself or another maize line. This invention further relates to hybrid maize seeds and plants produced by crossing the inbred line NP2015 with another maize line.

The invention is also directed to inbred maize line NP2015 into which one or more specific, single gene traits, for example transgenes, have been introgressed from another maize line and which have essentially all of the morphological and physiological characteristics of inbred maize line of NP2015, in addition to the one or more specific, single gene traits introgressed into the inbred. The invention also relates to seeds of an inbred maize line NP2015 into which one or more specific, single gene traits have been introgressed and to plants of an inbred maize line NP2015 into which one or more specific, single gene traits have been introgressed. The invention further relates to methods for producing a maize plant by crossing plants of an inbred maize line NP2015 into which one or more specific, single gene traits have been introgressed with themselves or with another maize line. The invention also further relates to hybrid maize seeds and plants produced by crossing plants of an inbred maize line NP2015 into which one or more specific, single gene traits have been introgressed with another maize line.

DEFINITIONS

In the description and examples that follow, a number of terms are used herein. In order to provide a clear and consistent understanding of the specification and claims, including the scope to be given such terms, the following definitions are provided. Below are the descriptors used in the data tables included herein. All linear measurements are in centimeters unless otherwise noted.

| | |
|---|---|
| Heat units | (Max Temp(<=86 deg. F.) + Min Temp(>=50 deg. F.))/2 − 50 |
| EMRGN | Final number of plants per plot |
| KRTP | Kernel type: 1.sweet 2.dent 3.flint 4.flour 5.pop 6.ornamental 7.pipecorn 8.other |
| ERTLP | % Root lodging (before anthesis) |
| GRNSP | % Brittle snapping (before anthesis) |
| TBANN | Tassel branch angle of 2nd primary lateral branch (at anthesis) |
| LSPUR | Leaf sheath pubescence of second leaf above the ear (at anthesis) 1–9 (1 = none) |
| ANGBN | Angle between stalk and 2nd leaf above the ear (at anthesis) |
| CR2L | Color of 2nd leaf above the ear (at anthesis) |
| GLCR | Glume Color |
| GLCB | Glume color bars perpendicular to their veins (glume bands): 1.absent 2.present |
| ANTC | Anther color |
| PLQUR | Pollen Shed: 0–9 (0 = male sterile) |
| HU1PN | Heat units to 10% pollen shed |
| HUPSN | Heat units to 50% pollen shed |
| SLKC | Silk color |
| HU5SN | Heat units to 50% silk |
| SLK5N | Days to 50% silk in adapted zone |
| HU9PN | Heat units to 90% pollen shed |
| HUPLN | Heat units from 10% to 90% pollen shed |
| DA19 | Days from 10% to 90% pollen shed |
| LAERN | Number of leaves above the top ear node |
| MLWVR | Leaf marginal waves: 1–9 (1 = none) |
| LFLCR | Leaf longitudinal creases: 1–9 (1 = none) |
| ERLLN | Length of ear leaf at the top ear node |
| ERLWN | Width of ear leaf at the top ear node at the widest point |
| PLHCN | Plant height to tassel tip |
| ERHCN | Plant height to the top ear node |
| LTEIN | Length of the internode between the ear node and the node above |
| LTASN | Length of the tassel from top leaf collar to tassel tip |
| LTBRN | Number of lateral tassel branches that originate from the central spike |
| EARPN | Number of ears per stalk |
| APBRR | Anthocyanin pigment of brace roots: 1.absent 2.faint 3.moderate 4.dark |
| TILLN | Number of tillers per plant |
| HSKC | Husk color 25 days after 50% silk (fresh) |
| HSKD | Husk color 65 days after 50% silk (dry) |
| HSKTR | Husk tightness 65 days after 50% silk: 1–9 (1 = loose) |
| HSKCR | Husk extension: 1.short (ear exposed) 2.medium (8 cm) 3.long (8–10 cm) 4.very long (>10 cm) |
| HEPSR | Position of ear 65 days after 50% silk: 1.upright 2.horizontal 3.pendent |
| STGRP | % Staygreen at maturity |
| DPOPN | % dropped ears 65 days after anthesis |
| LRTRN | % root lodging 65 days after anthesis |
| HU25 | Heat units to 25% grain moisture |
| HUSG | Heat units from 50% silk to 25% grain moisture in adapted zone |
| DSGM | Days from 50% silk to 25% grain moisture in adapted zone |
| SHLNN | Shank length |
| ERLNN | Ear length |
| ERDIN | Diameter of the ear at the midpoint |
| EWGTN | Weight of a husked ear (grams) |
| KRRWR | Kernel rows: 1.indistinct 2.distinct |
| KRNAR | Kernel row alignment: 1.straight 2.slightly curved 3.curved |
| ETAPR | Ear taper: 1.slight 2.average 3.extreme |
| KRRWN | Number of kernel rows |
| COBC | Cob color |
| COBDN | Diameter of the cob at the midpoint |
| KRTP | Endosperm type: 1.sweet 2.extra sweet 3.normal 4.high amylose 5.waxy 6.high protein 7.high lysine 8.super sweet 9.high oil 10.other |
| KRCL | Hard endosperm color |
| ALEC | Aleurone color |
| ALCP | Aleurone color pattern: 1.homozygous 2.segregating |
| KRLNN | Kernel length (mm) |
| KRWDN | Kernel width (mm) |

-continued

| | |
|---|---|
| KRDPN | Kernel thickness (mm) |
| K100N | 100 kernel weight (grams) |
| KRPRN | % round kernels on 13/64 slotted screen |
| GRLSR | Grey leaf spot severity rating; 1=resistent, 9=susceptible. |
| INTLR | Intactness rating of plants at time of harvest; 1=all foliage intact, 9=all plants broken below the ear. |
| LRTLP | Percentage of plants lodged, leaning >30 degrees from vertical, but unbroken at harvest. |
| MST_P | Percent grain moisture at harvest. |
| SCLBR | Southern corn leaf blight severity rating; 1=resistent, 9=susceptible. |
| STKLP | Percentage of plants with stalks broken below the ear at time of harvest. |
| YBUAN | Grain yield expressed as bushels per acre adjusted to 15.5% grain moisture. |

DETAILED DESCRIPTION OF THE INVENTION

Inbred maize lines are typically developed for use in the production of hybrid maize lines. Inbred maize lines need to be highly homogeneous, homozygous and reproducible to be useful as parents of commercial hybrids. There are many analytical methods available to determine the homozygotic and phenotypic stability of these inbred lines. The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

Some of the most widely used of these laboratory techniques are Isozyme Electrophoresis and RFLPs as discussed in Lee, M., "Inbred Lines of Maize and Their Molecular Markers," The Maize Handbook, (Springer-Verlag, New York, Inc. 1994, at 423–432) incorporated herein by reference. Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless. Maize RFLP linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference. This study used 101 RFLP markers to analyze the patterns of 2 to 3 different deposits each of five different inbred lines. The inbred lines had been selfed from 9 to 12 times before being adopted into 2 to 3 different breeding programs. It was results from these 2 to 3 different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0–2% residual heterozygosity. Although this was a relatively small study, it can be seen using RFLPs that the lines had been highly homozygous prior to the separate strain maintenance.

Inbred maize line NP2015 is a yellow dent maize inbred that is best suited as a male in crosses for producing first generation F1 maize hybrids. Inbred maize line NP2015 is best adapted to the Northwest, Northcentral and Northeast regions of the United States and the Corn Belt region of Canada and can be used to produce hybrids from approximately 92–100 relative maturity based on the Comparative Relative Maturity Rating System for harvest moisture of grain. Inbred maize line NP2015 demonstrates reliable late season plant health and good pollen shed. In hybrid combinations, NP2015 demonstrates high yield for its maturity, above average seedling vigor, medium plant stature, above average plant health, and has an attractive plant appearance. In hybrid combinations, NP2015 also demonstrates above average resistance to Northern Leaf Blight, average resistance to Eyespot, and superior resistance to first and second generations of European Corn Borer. For its area of adaptation, NP2015 demonstrates high yields, resistance to leaf diseases, consistent late season plant health, and reliable seedling vigor.

Inbred maize line NP2015 was derived from the cross of inbred line 807 and inbred line L8754. Both of the parents of NP2015 were developed and are owned by Novartis Seeds, Inc. Inbred line 807 is proprietary. Inbred line L8754 was selfed from the Pioneer hybrid 3790. After development of the $S_0$ (or $F_2$) population of 807×L8754, the breeding method was simple pedigree ear-to-row development of inbred NP2015. Inbred maize line NP2015 has shown uniformity and stability within the limits of environmental influence for all the traits as described in the Variety Description Information (Table 1) that follows. The inbred has been self-pollinated and ear-rowed a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in NP2015. Inbred maize line NP2015, being substantially homozygous, can be reproduced by planting seeds of the line, growing the resulting maize plants under self-pollinating or sib-pollinating conditions with adequate isolation, and harvesting the resulting seed, using techniques familiar to the agricultural arts.

The production of hybrid maize lines typically comprises planting in pollinating proximity seeds of, for example, inbred maize line NP2015 and of a different inbred parent maize plant, cultivating the seeds of inbred maize line NP2015 and of said different inbred parent maize plant into plants that bear flowers, emasculating the male flowers of inbred maize line NP2015 or the male flowers of said different inbred parent maize plant to produce an emasculated maize plant, allowing cross-pollination to occur between inbred maize line NP2015 and said different inbred parent maize plant and harvesting seeds produced on said emasculated maize plant. The harvested seed are grown to produce hybrid maize plants.

Inbred maize line NP2015 can be crossed to inbred maize lines of various heterotic group (see e.g. Hallauer et al. (1988) in Corn and Corn Improvement, Sprague et al, eds, chapter 8, pages 463–564, incorporated herein by reference) for the production of hybrid maize lines.

TABLE 1

VARIETY DESCRIPTION INFORMATION
Inbred maize line NP2015 is compared inbred CM105

| | INBRED NP2015 | | | INBRED CM105 | | |
|---|---|---|---|---|---|---|
| MATURITY | Days | Heat Units | | Days | Heat Units | |
| From emergence to 50% of plants in silk | 63 | 1202.6 | | 63 | 1180.9 | |
| From emergence to 50% of plants in pollen | 63 | 1196.6 | | 62 | 1160.8 | |
| From 10% to 90% pollen shed | 3 | 57.3 | | 3 | 59.4 | |
| PLANT | | Std Dev | Sample Size | | Std Dev | Sample Size |
| cm Plant Height (to tassel tip) | 162.7 | 18.32 | 55 | 171.4 | 16.56 | 50 |
| cm Ear Height (to base of top ear node) | 64 | 7.32 | 55 | 59.4 | 8.3 | 50 |
| cm Length of Top Ear Internodenode | 11.1 | 1.77 | 11 | 12.6 | 1.98 | 10 |
| Average Number of Tillers | .3 | .71 | 9 | .1 | .35 | 8 |
| Average Number of Ears per Stalk | 1.3 | .47 | 11 | 1.2 | .37 | 10 |
| Anthocyanin of Brace Roots: | 3 | | | 3 | | |
| 1 = Absent 2 = Faint | | | | | | |
| 3 = Moderate 4 = Dark | | | | | | |
| LEAF | | Std Dev | Sample Size | | Std Dev | Sample Size |
| cm Width of Ear Node Leaf | 9 | .75 | 55 | 7.6 | .62 | 10 |
| cm Length of Ear Node Leaf | 67 | 8.77 | 55 | 79.2 | 6.78 | |
| Number of leaves above top ear | 6 | .4 | 55 | 6 | .85 | 10 |
| degrees Leaf Angle | 41 | 13.64 | 9 | 49 | 11.8 | 7 |
| (measure from 2nd leaf above ear at anthesis to stalk above leaf) | | | | | | |
| Leaf Color | 3 | (Munsell code 5GY 4/6) | | 3 | (Munsell code 5GY 4/6) | |
| Leaf Sheath Pubescence | 3 | | | 6 | | |
| (Rate on scale from 1 + none to 9 = like peach fuzz) | | | | | | |
| Marginal Waves | 6 | | | 6 | | |

TABLE 1-continued

VARIETY DESCRIPTION INFORMATION
Inbred maize line NP2015 is compared inbred CM105

| | INBRED NP2015 | | | INBRED CM105 | | |
|---|---|---|---|---|---|---|
| (Rate on scale from 1 = none to 9 = many) | | | | | | |
| Longitudinal Creases | 3 | | | 3 | | |
| (Rate on scale from 1 = none to 9 = many) | | | | | | |
| TASSEL | | Std Dev | Sample Size | | Std Dev | Sample Size |
| Number of Primary Lateral Branches | 8 | 1.6 | 11 | 5 | 2.37 | 10 |
| Branch Angle from Central Spike | 41 | 11.5 | 10 | 45 | 8.02 | 8 |
| Cm Tassel Length | 23.6 | 10.09 | 11 | 32.2 | 3.33 | 8 |
| (from top leaf collar to tassel tip) | | | | | | |
| Pollen Shed | 6 | | | 6 | | |
| (Rate on scale from 0 = male sterile to 9 = heavy shed) | | | | | | |
| Anther Color | 6 | (Munsell code 5Y 8/6) | | 5 | (Munsell code 2.5GY 7/4) | |
| Glume Color | 5 | (Munsell code SGY 6/8) | | 2 | (Munsell code SGY 5/6) | |
| Bar Glumes (Glume Bands): 1 = Absent 2 = Present | 1 | | | 1 | | |
| EAR (Unhusked Data) | | | | | | |
| Silk Color (3 days after emergence) | 16 | (Munsell code 5RP 6/8) | | 5 | (Munsell code 2.5GY 8/10) | |
| Fresh Husk Color (25 days after 50% silking) | 1 | (Munsell code 2.5GY 7/6) | | 2 | (Munsell code 5GY 6/8) | |
| Dry Husk Color (65 days after 50% silking) | 7 | (Munsell code 2.5Y 7/10) | | 22 | (Munsell code 2.5Y 8/6) | |
| Position of Ear at Dry Husk Stage: | 1 | | | 3 | | |
| 1 = Upright 2 = Horizontal 3 = Pendent | | | | | | |
| Husk Tightness | 4 | | | 4 | | |
| (Rate on scale from 1 = very loose to 9 = very tight) | | | | | | |
| Husk Extension (at harvest): | 2 | | | 2 | | |
| 1 = Short (ears exposed) 2 = Medium (<8 cm) 3 = Long (8–10 cm beyond ear tip) 4 = Very long (>10 cm) | | | | | | |
| EAR (Husked Ear Data) | | Std Dev | Sample Size | | Std Dev | Sample Size |
| cm Ear Length | 14.8 | 1.64 | 11 | 13.3 | 2.07 | 9 |
| mm Ear Diameter at mid-point | 39.3 | 2.06 | 11 | 35.2 | 2.2 | 9 |
| gm Ear Weight | 119.7 | 27.38 | 11 | 80.5 | 21.19 | 9 |
| Number of Kernel Rows | 12 | 1.13 | 11 | 13 | 1.49 | 9 |
| Kernel Rows: 1 = Indistinct 2 = Distinct | 2 | | | 2 | | |
| Row Alignment: | 1 | | | 1 | | |
| 1 = Straight 2 = Slightly Curved 3 = Spiral | | | | | | |
| cm Shank Length | 11.5 | 4.44 | 11 | 9.2 | 3.12 | 9 |
| Ear Taper: 1 = Slight 2 = Average 3 = Extreme | 2 | | | 2 | | |
| KERNEL (Dried) | | Std Dev | Sample Size | | Std Dev | Sample Size |
| mm Kernel Length | 11.3 | .65 | 11 | 9.3 | 1 | 9 |
| mm Kernel Width | 8.7 | .47 | 11 | 7.6 | .53 | 9 |
| mm Kernel Thickness | 3.8 | .6 | 11 | 4 | .5 | 9 |
| % Round Kernels (Shape Grade) | 18.4 | 9.3 | 11 | 22.7 | 17.35 | 9 |
| Aleurone Color Pattern: | 1 | | | 1 | | |
| 1 = Homozygous 2 = Segregating | | | | | | |
| Aleurone Color | 12 | (Munsell code 5YR 7/6) | | 10 | (Munsell code 5YR 7/6) | |
| Hard Endosperm Color | 8 | (Munsell code 7.5YR 6/10) | | 8 | (Munsell code 7.5YR 6/10) | |
| Endosperm Type: | 3 | | | 3 | | |
| 1 = Sweet (sul) 2 = Extra Sweet (sh2) 3 = Normal Starch | | | | | | |
| gm Weight per 100 Kernels (unsized sample) | 32 | 4.32 | 11 | 21.6 | 5.39 | 9 |
| COB | | Std Dev | Sample Size | | Std Dev | Sample Size |
| mm Cob Diameter at mid-point | 24.5 | 1.69 | 11 | 24.8 | 1.53 | 9 |
| Cob Color | 12 | (Munsell code 10R 6/6) | | 12 | (Munsell code 10R 5/6) | |
| DISEASE RESISTANCE | | | | | | |
| (Rate from 1 (most susceptible) to 9 (most resistant)) | | | | | | |
| Leaf Blights, Wilts, and Local Infection Diseases | | | | | | |
| Eyespot (*Kabatiella zeae*) | 5 | | | 5 | | |
| Northern Leaf Blight (*Exserohilium turcicum*) | 3 | Race 1 | | 8 | Race 1 | |
| AGRONOMIC TRAITS | | | | | | |
| Stay Green (at 65 days after anthesis) | 6 | | | 2 | | |
| (rate on scale from 1 = worst to 9 = excellent) | | | | | | |
| % Dropped Ears (at 65 days after anthesis) | 0 | | | .3 | | |
| % Pre-anthesis Brittle snapping | 0 | | | .5 | | |

TABLE 1-continued

VARIETY DESCRIPTION INFORMATION
Inbred maize line NP2015 is compared inbred CM105

|  | INBRED NP2015 | INBRED CM105 |
|---|---|---|
| % Pre-anthesis Root Lodging | 0 | 0 |
| % Post-anthesis Root Lodging | 8 | 12 |
| (at 65 days after anthesis) | | |

In interpreting the foregoing color designations, reference may be had to be made to the Munsell Glossy Book of Color, a standard color reference. Color codes: 1.light green, 2.medium green, 3.dark green, 4.very dark green, 5.green-yellow, 6.pale yellow, 7.yellow, 8.yelow-orange, 9.salmon, 10.pink-orange, 11.pink, 12.light red, 13.cherry red, 14.red, 15.red and white, 16.pale purple, 17.purple, 18.colorless, 19.white, 20.white capped, 21.buff, 22.tan, 23.brown, 24.bronze, 25.variegated, 26.other.
Std Dev = Standard Deviation The invention also encompasses plants of inbred maize line NP2015 and parts thereof further comprising one or more specific, single gene traits which have been introgressed inbred maize line NP2015 from another maize line. Preferably, one or more new traits are transferred to inbred maize line NP2015, or, alternatively, one or more traits of inbred maize line NP2015 are altered or substituted. The transfer (or introgression) of the trait(s) into inbred maize line NP2015 is for example achieved by recurrent selection breeding, for example by backcrossing. In this case, inbred maize line NP2015 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172–175; Fehr (1987) Principles of Cultivar Development, Vol. 1: Theory and Technique, 360–376, incorporated herein by reference).

The laboratory-based techniques described above, in particular RFLP and SSR, are routinely used in such backcrosses to identify the progenies having the highest degree of genetic identity with the recurrent parent. This permits to accelerate the production of inbred maize lines having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity is based on molecular markers used in the laboratory-based techniques described above. Such molecular markers are for example those described in Boppenmaier, et al., "Comparisons among strains of inbreds for RFLPs", Maize Genetics Cooperative Newsletter (1991) 65, pg. 90, incorporated herein by reference, or those available from the University of Missouri database and the Brookhaven laboratory database (see http://www.agron.missouri.edu, incorporated herein by reference). The last backcross generation is then selfed to give pure breeding progeny for the gene(s) being transferred The resulting plants have essentially all of the morphological and physiological characteristics of inbred maize line NP2015, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

Many traits have been identified that are not regularly selected for in the development of a new inbred but that can be improved by backcrossing techniques. Examples of traits transferred to inbred maize line NP2015 include, but are not limited to, waxy starch, herbicide tolerance, resistance for bacterial, fungal, or viral disease, insect resistance, enhanced nutritional quality, improved performance in an industrial process, altered reproductive capability, such as male sterility or male fertility, yield stability and yield enhancement. Other traits transferred to inbred maize line NP2015 are for the production of commercially valuable enzymes or metabolites in plants of inbred maize line NP2015. Traits transferred to maize inbred line NP2015 are naturally occurring maize traits or are transgenic. Transgenes are originally introduced into a donor, non-recurrent parent using genetic engineering and transformation techniques well known in the art. A transgene introgressed into maize inbred line NP2015 typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements such as for example translation enhancers or termination signals. In a preferred embodiment, the nucleotide sequence is the coding sequence of a gene and is transcribed and translated into a protein. In another preferred embodiment, the nucleotide sequence encodes an antisense RNA or a sense RNA that is not translated or only partially translated.

Where more than one trait are introgressed into inbred maize line NP2015, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of inbred maize line NP2015 in addition to the multiple genes in the resulting maize inbred line.

The genes responsible for a specific, single gene trait are generally inherited through the nucleus. Known exceptions are, e.g. the genes for male sterility, some of which are inherited cytoplasmically, but still act as single gene traits. In a preferred embodiment, a transgene to be introgressed into maize inbred line NP2015 is integrated into the nuclear genome of the donor, non-recurrent parent. In another preferred embodiment, a transgene to be introgressed into maize inbred line NP2015 is integrated into the plastid genome of the donor, non-recurrent parent.

In a preferred embodiment, a transgene whose expression results or contributes to a desired trait to be transferred to maize inbred line NP2015 comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559–64, incorporated herein by reference). In another preferred embodiment, a transgene comprises a gene encoding an insecticidal protein, such as, for example, a crystal protein of *Bacillus thuringiensis* or a vegetative insecticidal protein from Bacillus cereus, such as VIP3 (see for example Estruch et al. Nat Biotechnol (1997) 15:137–41, incorporated herein by reference). In a preferred embodiment, an insecticidal gene introduced into maize inbred line NP2015 is a Cry1Ab gene or a portion thereof, for example introgressed into maize inbred line NP2015 from a maize line comprising a Bt-11 event as described in PCT/US98/04984, incorporated herein by reference, or from a maize line comprising a 176 event as described in Koziel et al. (1993) Biotechnology 11: 194–200, incorporated herein by reference. In yet another preferred embodiment, a transgene introgressed into maize inbred line NP2015 comprises a herbicide tolerance gene. For example, expression of an altered acetohydroxyacid synthase (AHAS) enzyme confers upon plants tolerance to various imidazolinone or sulfonamide herbicides (U.S. Pat. No. 4,761,373, incorporated herein by reference). In another preferred embodiment, a non-transgenic trait conferring tolerance to imidazolinones is introgressed into maize inbred line NP2015 (e.g a "IT" or "IR" trait). U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoximine. Also, expression of a Streptomyces bar gene encoding a phosphinothricin acetyl transferase in maize plants results in tolerance to the herbicide phosphinothricin or gluphosinate (U.S. Pat. No. 5,489,520, incorporated herein by reference). U.S. Pat. No. 5,013,659, incorporated herein by reference, is directed to plants that express a mutant acetolactate synthase (ALS) that renders the plants resistant to inhibition by sulfonylurea herbicides. U.S. Pat. No. 5,162,602, incorporated herein by reference, discloses plants tolerant to inhibition by cyclohexanedione and aryloxyphenoxypropanoic acid herbicides. The tolerance is conferred by an altered acetyl coenzyme A carboxylase(ACCase). U.S. Pat. No. 5,554,798, incorporated herein by reference, discloses transgenic glyphosate tolerant maize plants, which tolerance is conferred by an altered 5-enolpyruvyl-3-phosphoshikimate (EPSP) synthase gene. Also, tolerance to a protoporphyrinogen oxidase inhibitor is achieved by expression of a tolerant protoporphyrinogen oxidase enzyme in plants (U.S. Pat. No. 5,767,373, incorporated herein by reference).

In a preferred embodiment, a transgene introgressed into maize inbred line NP2015 comprises a gene conferring tolerance to a herbicide and at least another nucleotide sequence encoding another trait, such as for example, an insecticidal protein. Such combination of single gene traits is for example a Cry1Ab gene and a bar gene. Specific transgenic events introgressed into maize inbred line NP2015 are found at http://www.aphis.usda.gov/bbep/bp/not_reg.html, incorporated herein by reference. These are for example introgressed from glyphosate tolerant event GA21 (application number 9709901p), glyphosate tolerant/ Lepidopteran insect resistant event MON 802 (application number 9631701p), Lepidopteran insect resistant event DBT418 (application number 9629101p), male sterile event MS3 (application number 9522801p), Lepidopteran insect resistant event Bt11 (application number 9519501p), phosphinothricin tolerant event B16 (application number 9514501 p), Lepidopteran insect resistant event MON 80100 (application number 9509301p), phosphinothricin tolerant events T14, T25 (application number 9435701p), Lepidopteran insect resistant event 176 (application number 9431901p).

The introgression of a Bt11 event into a maize line, such as maize inbred line NP2015, by backcrossing is exemplified in PCT/US98/04984, incorporated herein by reference, and the present invention is directed to methods of introgressing a Bt11 event into maize inbred line NP2015 using for example the markers described in PCT/US98/04984 and to resulting maize lines.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which do not have the desired herbicide tolerance characteristic, and only those plants which have the herbicide tolerance gene are used in the subsequent backcross. This process is then repeated for the additional backcross generations.

INDUSTRIAL APPLICABILITY

This invention also is directed to methods for producing a maize plant by crossing a first parent maize plant with a second parent maize plant wherein either the first or second parent maize plant is a maize plant of inbred line NP2015 or a maize plant of inbred line NP2015 further comprising one or more single gene traits. Further, both first and second parent maize plants can come from the inbred maize line NP2015 or an inbred maize plant of NP2015 further comprising one or more single gene traits. Thus, any such methods using the inbred maize line NP2015 or an inbred maize plant of NP2015 further comprising one or more single gene traits are part of this invention: selfing, backcrosses, hybrid production, crosses to populations, and the like. All plants produced using inbred maize line NP2015 or inbred maize plants of NP2015 further comprising one or more single gene traits as a parent are within the scope of this invention. Advantageously, inbred maize line NP2015 or inbred maize plants of NP2015 further comprising one or more single gene traits are used in crosses with other, different, maize inbreds to produce first generation (F1) maize hybrid seeds and plants with superior characteristics.

In a preferred embodiment, seeds of inbred maize line NP2015 or seeds of inbred maize plants of NP2015 further comprising one or more single gene traits are provided as an essentially homogeneous population of inbred corn seeds. Essentially homogeneous populations of inbred seed are those that consist essentially of the particular inbred seed, and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs. The population of inbred corn seeds of the invention is further particularly defined as being essentially free from hybrid seed. The inbred seed population may be separately grown to provide an essentially homogeneous population of plants of inbred maize line NP2015 or inbred maize plants of NP2015 further comprising one or more single gene traits.

As used herein, the term "plant" includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk, seeds and the like. Duncan, Williams, Zehr, and Widholm, Planta (1985) 165:322–332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262–265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64–65 (1986), refers to somatic embryogenesis from glume callus cultures and B. V. Conger, et al., Plant Cell Reports, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," Maize for Biological Research (Plant Molecular Biology Association, Charlottesville, Va. 1982, at 367–372) and in Duncan, et al., "The Production of Callus Capable of Plant Regeneration from Immature Embryos of Numerous Zea mays Genotypes," 165 Planta 322–332 (1985). Thus, another aspect of this invention is to provide cells which upon growth and differentiation produce maize plants having the physiological and morphological characteristics of inbred maize line NP2015. In a preferred embodiment, cells of inbred maize line NP2015 are transformed genetically, for example with one or more genes described above, for example by using a transformation method described in PCT/US98/04984, incorporated herein by reference, and transgenic plants of inbred maize line NP2015 are obtained and used for the production of hybrid maize plants.

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of inbred maize line NP2015 or of inbred maize line NP2015 further comprising one or more single gene traits, the plant produced from the inbred seed, the hybrid maize plant produced from the crossing of the inbred, hybrid seed, and various parts of the hybrid maize plant can be utilized for human food, livestock feed, and as a raw material in industry.

PERFORMANCE EXAMPLES OF MAIZE
INBRED LINE NP2015

In the examples that follow, the traits and characteristics of inbred maize line NP2015 are presented as an inbred comparisons per se and as inbred by tester comparisons. The data presented is for key characteristics and traits and is reported from experiments where the compared lines where grown side-by-side.

Inbred Comparisons

The data in table 2A show for example that inbred NP2015 is significantly higher to the top ear node than inbred A619, that inbred NP2015 has significantly shorter tassel from top leaf collar to tassel tip than inbred A619, that inbred NP2015 has significantly thinner kernels than inbred A619, that inbred NP2015 has significantly less round kernels on 13/64 slotted screen than inbred A619 and that inbred NP2015 has significantly less leaf longitudinal creases than inbred A619.

TABLE 2A

Comparison of inbreds NP2015 and A619

|  | PLHCN | ERHCN | HU1SN | HU5SN | HU9SN | HUPSN | HUPLN | PLQUR | EARPN | SHLNN | LTEIN | ERLWN |
|---|---|---|---|---|---|---|---|---|---|---|---|---|
| NP2015 | 168 | 66 | 1181 | 1212 | 1239 | 1202 | 46 | 6 | 1 | 10 | 10 | 9 |
| A619 | 168 | 41 | 1227 | 1308 | 1296 | 1257 | 55 | 7 | 1 | 8 | 12 | 10 |
| Grand Mean | 168 | 54 | 1204 | 1260 | 1268 | 1230 | 50 | 6 | 1 | 9 | 11 | 9 |
| Trials w/data | 3 | 3 | 3 | 3 | 3 | 3 | 3 | 3 | 3 | 3 | 3 | 3 |
| LSD | 56 | 15 | 80 | 135 | 83 | 68 | 19 | 1 | 0 | 3 | 9 | 2 |
| CV % | 6 | 24 | 1 | 1 | 1 | 1 | 39 | 13 | 20 | 33 | 11 | 20 |
| Probability % | 98 | 0 | 13 | 9 | 10 | 8 | 34 | 8 | 0 | 25 | 52 | 60 |

|  | ERLLN | LAERN | ANGBN | LTBRN | TBANN | LTASN | ERLNN | ERDIN | EWGTN | KRRWN | KRLNN | KRWDN |
|---|---|---|---|---|---|---|---|---|---|---|---|---|
| NP2015 | 67 | 5 | 38 | 8 | 45 | 28 | 15 | 39 | 118 | 12 | 11 | 9 |

TABLE 2A-continued

Comparison of inbreds NP2015 and A619

| A619 | 69 | 5 | 38 | 8 | 41 | 39 | 13 | 39 | 89 | 13 | 11 | 9 |
|---|---|---|---|---|---|---|---|---|---|---|---|---|
| Grand Mean | 68 | 5 | 38 | 8 | 43 | 33 | 14 | 39 | 103 | 13 | 11 | 9 |
| Trials w/data | 3 | 3 | 3 | 3 | 3 | 3 | 3 | 3 | 3 | 3 | 3 | 3 |
| LSD | 15 | 4 | 8 | 7 | 13 | 2 | 12 | 25 | 106 | 7 | 1 | 1 |
| CV % | 3 | 13 | 19 | 18 | 27 | 6 | 7 | 9 | 13 | 11 | 6 | 8 |
| Probability % | 64 | 86 | 98 | 81 | 59 | 0 | 52 | 91 | 37 | 49 | 72 | 92 |

| | KRDPN | KRPRN | K100N | COBDN | APBRR | LSPUR | MLWVR | LFLCR | HEPSR | KRNAR | ETAPR |
|---|---|---|---|---|---|---|---|---|---|---|---|
| NP2015 | 4 | 19 | 33 | 24 | 3 | 3 | 6 | 3 | 1 | 2 | 2 |
| A619 | 5 | 61 | 32 | 27 | 2 | 2 | 6 | 5 | 1 | 2 | 2 |
| Grand Mean | 4 | 40 | 33 | 25 | 3 | 2 | 6 | 4 | 1 | 2 | 2 |
| Trials w/data | 3 | 3 | 3 | 3 | 3 | 3 | 3 | 3 | 3 | 3 | 3 |
| LSD | 1 | 15 | 4 | 16 | 1 | 4 | 1 | 1 | 1 | 0 | 0 |
| CV % | 18 | 33 | 10 | 8 | 12 | 33 | 16 | 26 | 27 | 4 | 19 |
| Probability % | 0 | 0 | 42 | 55 | 18 | 23 | 38 | 0 | 42 | 0 | 11 |

The data in table 2B show for example that inbred NP2015 is significantly shorter to the top ear node than inbred B64, that inbred NP2015 is shedding pollen and extruding silk significantly earlier than inbred B64 and that inbred NP2015 has a significantly shorter tassel from top leaf collar to tassel tip than inbred B64.

from top leaf collar to tassel tip than inbred CM105, that inbred NP2015 has significantly longer kernels than inbred CM105, that inbred NP2015 has significantly wider kernels than inbred CM105, that inbred NP2015 has significantly heavier kernels than inbred CM105 and that inbred NP2015 has a significantly less leaf sheath pubescence of second leaf

TABLE 2B

Comparison of inbreds NP2015 and B64

| | LRTLP | PLHCN | ERHCN | HU1SN | HU5SN | HU9SN | HUPSN | STGRP | HUPLN | PLQUR | EARPN | LTEIN | ERLWN |
|---|---|---|---|---|---|---|---|---|---|---|---|---|---|
| NP2015 | 11 | 168 | 66 | 1181 | 1212 | 1239 | 1202 | 6 | 46 | 6 | 1 | 10 | 9 |
| B64 | 50 | 212 | 95 | 1510 | 1552 | 1590 | 1549 | 8 | 60 | 5 | 1 | 13 | 8 |
| Grand Mean | 27 | 190 | 80 | 1312 | 1348 | 1380 | 1341 | 7 | 52 | 6 | 1 | 12 | 9 |
| Trials w/data | 3 | 3 | 3 | 3 | 3 | 3 | 3 | 2 | 3 | 3 | 3 | 3 | 3 |
| LSD | 29 | 47 | 15 | | | | | 32 | 19 | 19 | 2 | 8 | 2 |
| CV % | 81 | 5 | 16 | | | | | 0 | 39 | 14 | 18 | 11 | 21 |
| Probability % | 2 | 6 | 0 | 0 | 0 | 0 | 0 | 50 | 17 | 65 | 82 | 29 | 57 |

| | ERLLN | LAERN | ANGBN | LTBRN | TBANN | LTASN | APBRR | LSPUR | MLWVR | LFLCR | HSKTR | HEPSR |
|---|---|---|---|---|---|---|---|---|---|---|---|---|
| NP2015 | 67 | 5 | 38 | 8 | 45 | 28 | 3 | 3 | 6 | 3 | 5 | 1 |
| B64 | 95 | 5 | 45 | 7 | 46 | 44 | 3 | 7 | 6 | 2 | 9 | 1 |
| Grand Mean | 81 | 5 | 41 | 7 | 46 | 36 | 3 | 5 | 6 | 3 | 7 | 1 |
| Trials w/data | 3 | 3 | 3 | 3 | 3 | 3 | 3 | 3 | 3 | 3 | 2 | 3 |
| LSD | 16 | 1 | 8 | 2 | 13 | 2 | 3 | 15 | 1 | 1 | 13 | 1 |
| CV % | 3 | 12 | 18 | 19 | 26 | 5 | 11 | 17 | 17 | 39 | 0 | 27 |
| Probability % | 2 | 17 | 16 | 34 | 87 | 0 | 84 | 21 | 25 | 56 | 16 | 42 |

The data in table 2C show for example that inbred NP2015 is shedding pollen significantly later than inbred CM105, that inbred NP2015 has significantly shorter tassel above the ear (at anthesis) than inbred CM105.

TABLE 2C

Comparison of inbreds NP2015 and CM105

| | PLHCN | ERHCN | HU1SN | HU5SN | HU9SN | HUPSN | HUPLN | PLQUR | EARPN | SHLNN | HSKCR | LTEIN |
|---|---|---|---|---|---|---|---|---|---|---|---|---|
| NP2015 | 168 | 66 | 1181 | 1212 | 1239 | 1202 | 46 | 6 | 1 | 10 | 2 | 10 |
| CM105 | 174 | 62 | 1116 | 1183 | 1186 | 1152 | 57 | 6 | 1 | 8 | 3 | 12 |
| Grand Mean | 171 | 64 | 1149 | 1197 | 1213 | 1177 | 52 | 6 | 1 | 9 | 3 | 11 |
| Trials w/data | 3 | 3 | 3 | 3 | 3 | 3 | 3 | 3 | 3 | 3 | 2 | 3 |
| LSD | 12 | 15 | 16 | 212 | 19 | 16 | 19 | 1 | 0 | 3 | 13 | 9 |
| CV % | 6 | 20 | 1 | 1 | 1 | 1 | 38 | 14 | 19 | 32 | 0 | 12 |
| Probability % | 35 | 55 | 0 | 62 | 0 | 0 | 22 | 49 | 2 | 30 | 50 | 53 |

| | ERLWN | ERLLN | LAERN | ANGBN | LTBRN | TBANN | LTASN | ERLNN | ERDIN | EWGTN | KRRWN | KRLNN |
|---|---|---|---|---|---|---|---|---|---|---|---|---|

TABLE 2C-continued

Comparison of inbreds NP2015 and CM105

| | | | | | | | | | | | | |
|---|---|---|---|---|---|---|---|---|---|---|---|---|
| NP2015 | 9 | 67 | 5 | 38 | 8 | 45 | 28 | 15 | 39 | 118 | 12 | 11 |
| CM105 | 8 | 80 | 5 | 51 | 7 | 47 | 34 | 13 | 34 | 77 | 13 | 10 |
| Grand Mean | 8 | 73 | 5 | 45 | 7 | 46 | 31 | 14 | 37 | 97 | 13 | 10 |
| Trials w/data | 3 | 3 | 3 | 3 | 3 | 3 | 3 | 3 | 3 | 3 | 3 | 3 |
| LSD | 2 | 11 | 1 | 38 | 2 | 13 | 2 | 10 | 4 | 73 | 2 | 1 |
| CV % | 22 | 3 | 13 | 17 | 20 | 25 | 6 | 7 | 10 | 14 | 11 | 6 |
| Probability % | 18 | 4 | 70 | 29 | 19 | 77 | 0 | 46 | 5 | 14 | 28 | 0 |

| | KRWDN | KRDPN | KRPRN | K100N | COBDN | APBRR | LSPUR | MLWVR | LFLCR | HSKTR | HEPSR |
|---|---|---|---|---|---|---|---|---|---|---|---|
| NP2015 | 9 | 4 | 19 | 33 | 24 | 3 | 3 | 6 | 3 | 5 | 1 |
| CM105 | 8 | 4 | 31 | 25 | 24 | 3 | 6 | 5 | 4 | 4 | 2 |
| Grand Mean | 8 | 4 | 25 | 29 | 24 | 3 | 5 | 6 | 3 | 4 | 2 |
| Trials w/data | 3 | 3 | 3 | 3 | 3 | 3 | 3 | 3 | 3 | 2 | 3 |
| LSD | 1 | 1 | 15 | 4 | 2 | 2 | 1 | 1 | 1 | 44 | 4 |
| CV % | 9 | 19 | 51 | 12 | 9 | 10 | 17 | 17 | 30 | 0 | 17 |
| Probability % | 0 | 19 | 9 | 0 | 79 | 74 | 0 | 3 | 8 | 74 | 42 |

Inbred By Tester Comparison

The results in Table 3A compare inbred NP2015 and inbreda when each inbred is crossed to the same tester line. For example, the NP2015 hybrid has significantly higher grain yield expressed as bushels per acre adjusted to 15.5% grain moisture than the inbredA hybrid, the NP2015 hybrid has significantly higher grain moisture at harvest than the inbredA hybrid, the NP2015 hybrid has significantly more emerged plants prior to thinning than the inbredA hybrid.

For example, the NP2015 hybrid has significantly higher grain yield expressed as bushels per acre adjusted to 15.5% grain moisture than the inbredB hybrid, the NP2015 hybrid has significantly higher grain moisture at harvest than the inbredB hybrid, the NP2015 hybrid has a significantly higher % stand than the inbredB hybrid, the NP2015 hybrid has significantly more emerged plants prior to thinning than the inbredB hybrid, the NP2015 hybrid is significantly later to shed pollen and extrude silk than the inbredA hybrid.

TABLE 3A

Comparison of inbred NP2015 crossed to tester inbredX and inbredA crossed to tester inbredX

| | YBUAN | MST_P | STD_P | EMRGP | STKLP | LRTLP | ERTLP | PLHCN | ERHCN | HU5SN |
|---|---|---|---|---|---|---|---|---|---|---|
| INBRED X/NP2015 | 155.6 | 22.2 | 97 | 93.4 | 1 | 0 | 3 | 227 | 94 | 1203 |
| INBRED X/INBRED A | 140.9 | 19.4 | 95 | 90.2 | 1 | 7 | 10 | 213 | 90 | 1190 |
| Grand Mean | 148.3 | 20.8 | 96 | 91.8 | 1 | 4 | 7 | 220 | 92 | 1196 |
| Trials w/data | 47 | 48 | 51 | 48 | 35 | 13 | 12 | 5 | 5 | 5 |
| LSD | 5 | 0.5 | 1 | 1.3 | 1 | 10 | 6 | 46 | 9 | 18 |
| CV % | 11.6 | 5.6 | 4 | 4.8 | 350 | 112 | 156 | 9 | 11 | 2 |
| Probability % | 0 | 0 | 1 | 0 | 64 | 16 | 3 | 44 | 32 | 15 |

| | HUPSN | INTLR | TSTWN | SVGRR | PLTAR | GRQUR | EMRGR | ERGRR |
|---|---|---|---|---|---|---|---|---|
| INBRED X/NP2015 | 1202 | 2.9 | 58.8 | 2.9 | 4 | 2.9 | 3.2 | 2.5 |
| INBRED X/INBRED A | 1181 | 3.4 | 59 | 4 | 2.5 | 2 | 4.1 | 3 |
| Grand Mean | 1191 | 3.2 | 58.9 | 3.5 | 3.3 | 2.5 | 3.7 | 2.8 |
| Trials w/data | 5 | 11 | 39 | 8 | 4 | 5 | 5 | 11 |
| LSD | 17 | 0.5 | 0.7 | 0.8 | 2.1 | 0.7 | 1 | 0.4 |
| CV % | 2 | 24.6 | 3.8 | 18.9 | 28.2 | 15.8 | 29.4 | 23.8 |
| Probability % | 1 | 4.4 | 64.8 | 1.6 | 10.2 | 2.1 | 5.9 | 0.6 |

STD_P: % Stand, EMRGP: % emerged plants prior to thinning, TSTWN: test weight in LBS/BU, SVGRR: seedling vigor (3–5 leaf stage), PLTAR: plant Appearance, GRQUR grain quality, EMRGR: early emergence vigor (prior to 3-leaf stage), ERGRR: early growth (6+ leaf stage).

The results in Table 3B compare inbred NP2015 and inbredB when each inbred is crossed to the same tester line.

TABLE 3B

Comparison of inbred NP2015 crossed to tester inbredX and inbredB crossed to tester inbredX

| | YBUAN | MST_P | STD_P | EMRGP | PLHCN | ERHCN | HU5SN | HUBLN | HUPSN | INTLR |
|---|---|---|---|---|---|---|---|---|---|---|
| INBRED X/NP2015 | 153.7 | 24.2 | 97 | 93.8 | 239 | 101 | 1185 | 1900 | 1187 | 3.2 |
| INBRED X/INBRED B | 144.9 | 23.1 | 95 | 89.8 | 246 | 93 | 1148 | 1926 | 1143 | 3.5 |

TABLE 3B-continued

Comparison of inbred NP2015 crossed to tester inbredX and inbredB crossed to tester inbredX

| | | | | | | | | | | |
|---|---|---|---|---|---|---|---|---|---|---|
| Grand Mean | 149.4 | 23.7 | 96 | 91.8 | 242 | 97 | 1167 | 1913 | 1165 | 3.4 |
| Trials w/data | 75 | 76 | 79 | 76 | 9 | 9 | 7 | 1 | 7 | 12 |
| LSD | 3.7 | 0.4 | 1 | 1 | 11 | 7 | 14 | 61 | 13 | 0.5 |
| CV % | 10.8 | 4.9 | 4 | 4.8 | 7 | 11 | 2 | 2 | 1 | 23.2 |
| Probability % | 0 | 0 | 0 | 0 | 19 | 3 | 0 | 1 | 0 | 18.4 |

| | TSTWN | STGRP | SVGRR | PLTAR | GRQUR | PSTSN | PSTSP | EMRGR | ERGRR | TWFKN |
|---|---|---|---|---|---|---|---|---|---|---|
| INBRED X/NP2015 | 59.4 | 34 | 3.2 | 3.9 | 2.9 | 0.6 | 15 | 9.5 | 2.8 | 62 |
| INBRED X/INBRED B | 60.3 | 42 | 3.1 | 2.6 | 2.1 | 9.7 | 27 | 9.9 | 3.3 | 65 |
| Grand Mean | 59.8 | 38 | 3.1 | 3.3 | 2.5 | 5.2 | 21 | 9.7 | 3 | 63 |
| Trials w/data | 60 | 3 | 14 | 7 | 8 | 2 | 36 | 9 | 16 | 3 |
| LSD | 0.6 | 11 | 0.3 | 2.1 | 0.3 | 6.4 | 10 | 1.5 | 0.5 | 1 |
| CV % | 3.7 | 25 | 20.7 | 45.5 | 11.7 | 88 | 101 | 12.3 | 21.2 | 2 |
| Probability % | 0.2 | 13 | 75 | 17.8 | 0 | 0.6 | 3 | 58 | 5 | 0 |

HUBLN: heat units to physiological maturity, PSTSN: push test for stalk/root quality on erect plants per row, PSTSP: push test for stalk/root quality on erect plants, TWFKN: test weight in Kg/Fix volume in cubic centimeter.

DEPOSIT

Applicants have made a deposit of at least 2500 seeds of Inbred Corn Line NP2015 with the American Type Culture Collection (ATCC), Manassas, Va., 20110-2209 U.S.A., ATCC Deposit No:203773. The seeds deposited with the ATCC on Feb. 12, 1999 were taken from the deposit maintained by Novartis Corporation, 3054 Cornwallis Road, Research Triangle Park, N.C. 27709, since prior to the filing date of this application. This deposit of the Inbred Maize Line NP2015 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.). U.S. Plant Variety Protection of Inbred Maize Line NP2015 has been applied for under application Ser. No. 9800391.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of maize inbred line NP2015 having been deposited under ATCC Accession No: 203773.
2. A maize plant, or parts thereof, of inbred line NP2015, seed of said line having been deposited under ATCC Accession No: 203773.
3. Pollen of the plant of claim 2.
4. An ovule of the plant of claim 2.
5. A maize plant, or parts thereof, having all the physiological and morphological characteristics of a plant of inbred line NP2015, seed of said line having been deposited under ATCC Accession No: 203773.
6. A male sterile maize plant, or parts thereof, otherwise having all the physiological and morphological characteristics of a plant of inbred line NP2015, seed of said line having been deposited under ATCC Accession No: 203773.
7. A maize plant, or parts thereof, of inbred line NP2015, seed of said line having been deposited under ATCC Accession No: 203773, further comprising one or more single gene transferred traits.
8. A maize plant according to claim 7, wherein said single gene transferred trait comprises a gene which is introduced by transgenic methods.
9. A maize plant according to claim 7, wherein said single gene transferred trait comprises a gene conferring upon said maize plant tolerance to a herbicide.
10. A maize plant according to claim 9, wherein said herbicide is glyphosate, glufosinate or a protoporphyrinogen oxidase inhibitor.
11. A maize plant according to claim 7, wherein said single gene transferred trait comprises a gene conferring upon said maize plant insect resistance, disease resistance or virus resistance.
12. A maize plant according to claim 11, wherein said gene conferring upon said maize plant insect resistance is a *Bacillus thuringiensis* Cry1Ab gene.
13. A maize plant according to claim 12, further comprising a bar gene.
14. A maize plant according to claim 12, wherein said Cry1Ab gene is introgressed into said maize plant from a maize line comprising a Bt-11 event or a 176 event.
15. A tissue culture of regenerable cells of a maize plant of inbred line NP2015, seed of said inbred line having been deposited under ATCC Accession No: 203773.
16. A tissue culture according to claim 15, the regenerable cells being selected from the group consisting of embryos, meristems, pollen, leaves, anthers, roots, root tips, silk, flowers, kernels, ears, cobs, husks and stalks, or being protoplasts or callus derived therefrom.
17. A maize plant regenerated from the tissue culture of claim 15, capable of expressing all the morphological and physiological characteristics of inbred line NP2015, seed of said inbred line having been deposited under ATCC Accession No: 203773.
18. A method for producing maize seed comprising crossing a first parent maize plant with a second parent maize plant and harvesting the resultant first generation maize seed, wherein said first or second parent maize plant is the inbred maize plant of claim 2.

19. A method according to claim 18, wherein said first parent maize plant is different from said second parent maize plant, wherein said resultant seed is a first generation (F1) hybrid maize seed.

20. A method according to claim 18, wherein inbred maize plant of claim 2 is the female parent.

21. A method according to claim 18, wherein inbred maize plant of claim 2 is the male parent.

22. An F1 hybrid seed produced by the method of claim 19.

23. An F1 hybrid plant, or parts thereof, grown from the seed of claim 22.

24. A method for producing maize seed comprising crossing a first parent maize plant with a second parent maize plant and harvesting the resultant first generation maize seed, wherein said first or second parent maize plant is the inbred maize plant of claim 5.

25. A method according to claim 24, wherein said first parent maize plant is different from said second parent maize plant, wherein said resultant seed is a first generation (F1) hybrid maize seed.

26. A method according to claim 24, wherein inbred maize plant of claim 5 is the female parent.

27. A method according to claim 26, wherein inbred maize plant of claim 5 is the male parent.

28. An F1 hybrid seed produced by the method of claim 25.

29. An F1 hybrid plant, or parts thereof, grown from the seed of claim 28.

30. A method for producing maize seed comprising crossing a first parent maize plant with a second parent maize plant and harvesting the resultant first generation maize seed, wherein said first or second parent maize plant is the inbred maize plant of claim 7.

31. A method according to claim 30, wherein said first parent maize plant is different from said second parent maize plant, wherein said resultant seed is a first generation (F1) hybrid maize seed.

32. A method according to claim 30, wherein inbred maize plant of claim 7 is the female parent.

33. A method according to claim 30, wherein inbred maize plant of claim 7 is the male parent.

34. An F1 hybrid seed produced by the method of claim 31.

35. An F1 hybrid plant, or parts thereof, grown from the seed of claim 34.

36. A method comprising:

(a) planting a collection of seed comprising seed of a hybrid, one of whose parents is inbred line NP2015, seed of said line having been deposited under ATCC Accession No: 203773, or a maize plant having all the physiological and morphological characteristics of inbred line NP2015, said collection also comprising seed of said inbred;

(b) growing plants from said collection of seed;

(c) identifying said inbred plants;

(d) selecting said inbred plant; and (e) controlling pollination in a manner which preserves the homozygosity of said inbred plant.

37. A method according to claim 36, wherein said one parent is inbred maize line NP2015, seed of said line having been deposited under ATCC Accession No: 203773, further comprising one or more single gene transferred traits.

38. The process of claim 36 wherein said step of identifying said inbred plant comprises:

identifying plants with decreased vigor.

39. A method comprising introgressing one or more single gene traits into inbred maize line NP2015, seed of said line having been deposited under ATCC Accession No: 203773, using one or more markers for marker assisted selection among maize lines to be used in a maize breeding program, the markers being associated with said one or more single gene traits, wherein the resulting maize line is inbred line NP2015 further comprising said one or more single gene transferred traits.

40. A method according to claim 39, wherein said one or more single gene traits comprises a Cry1Ab gene and said markers comprise Z1B3 and UMC150a.

41. A maize plant according to claim 7, wherein said single gene transferred trait comprises a gene which is first introduced by transgenic methods into a maize line different from said inbred maize line NP2015 and then introgressed into said inbred maize line NP2015.

42. Seeds of a plant according to claim 7.

* * * * *